US012805702B2

(12) United States Patent
Wataya

(10) Patent No.: US 12,805,702 B2
(45) Date of Patent: Nov. 24, 2026

(54) IMAGE PICKUP UNIT FOR ENDOSCOPE AND ENDOSCOPE

(71) Applicant: OLYMPUS MEDICAL SYSTEMS CORP., Tokyo (JP)

(72) Inventor: Yuichi Wataya, Akiruno (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 154 days.

(21) Appl. No.: 18/516,055

(22) Filed: Nov. 21, 2023

(65) Prior Publication Data

US 2024/0081621 A1 Mar. 14, 2024

Related U.S. Application Data

(63) Continuation of application No. PCT/JP2021/023356, filed on Jun. 21, 2021.

(51) Int. Cl.

*A61B 1/00* (2006.01)
*A61B 1/05* (2006.01)

(52) U.S. Cl.

CPC ............ *A61B 1/0011* (2013.01); *A61B 1/051* (2013.01)

(58) Field of Classification Search

CPC .. A61B 1/00188; G02B 23/2407–2438; G02B 7/04–105

See application file for complete search history.

(56) References Cited

U.S. PATENT DOCUMENTS 3,645,861 A * 2/1972 Garvey .................... C25D 5/36 428/685
10,739,548 B2 * 8/2020 Iguchi ...................... G02B 7/08
11,774,742 B2 * 10/2023 Ogi ........................ H02K 33/16 359/824
2003/0023143 A1 1/2003 Abe et al.
(Continued)

FOREIGN PATENT DOCUMENTS

EP 1 764 522 A2 3/2007
JP 2000-089136 A 3/2000
(Continued)

OTHER PUBLICATIONS

Takagi et al ("Lubrication of Bearing Steels With Electroplated Gold Under Heavy Loads", Air Force Materials Laboratory Technical Report AFML-TR-67-61, Mar. 1967) (Year: 1967).*
(Continued)

*Primary Examiner* — Leon W Rhodes, Jr.
(74) *Attorney, Agent, or Firm* — Scully, Scott, Murphy & Presser, P.C.

(57) ABSTRACT

An image pickup unit for endoscope includes a first barrel having first hardness, a second barrel having second hardness in which an optical member is internally provided, the second barrel being held in a hole of the first barrel to be movable, a film having third hardness formed on one of an inner surface of the hole and an outer surface of the second barrel, a magnet provided in the second barrel, and a coil provided in the first barrel and configured to generate a magnetic field that acts on the magnet. The second barrel has a magnet or is composed by a magnetic material. The second barrel slides in the first barrel according to energization to the coil. The third hardness is lower than the first hardness and the second hardness.

14 Claims, 5 Drawing Sheets

(56) References Cited

U.S. PATENT DOCUMENTS

| | | | |
|---|---|---|---|
| 2007/0003693 | A1 | 1/2007 | Lee et al. |
| 2007/0065067 | A1 | 3/2007 | Gartner et al. |
| 2015/0287508 | A1 | 10/2015 | Wieters et al. |

FOREIGN PATENT DOCUMENTS

| | | | | |
|---|---|---|---|---|
| JP | 2002-122795 | A | 4/2002 | |
| JP | 2002-345724 | A | 12/2002 | |
| JP | 2005-013277 | A | 1/2005 | |
| JP | 2007-092995 | A | 4/2007 | |
| JP | 2008-545065 | A | 12/2008 | |
| JP | 2009-232896 | A | 10/2009 | |
| JP | 2009-240709 | A | 10/2009 | |
| JP | 2015015246 | A | 1/2015 | |
| JP | 2016-509490 | A | 3/2016 | |
| JP | 2016-173421 | A | 9/2016 | |
| JP | 2018-066877 | A | 4/2018 | |
| KR | 101086847 | B1 * | 11/2011 | ............... C08K 3/32 |
| WO | 2007/004770 | A1 | 1/2007 | |
| WO | 2014/094970 | A1 | 6/2014 | |

OTHER PUBLICATIONS

English machine translation of Jp 2000-089136A (Year: 2000).*
International Search Report dated Aug. 3, 2021 received in PCT/JP2021/023356.

* cited by examiner

IMAGE PICKUP UNIT FOR ENDOSCOPE AND ENDOSCOPE

CROSS REFERENCE TO RELATED APPLICATION

This application is a continuation application of PCT/JP2021/023356 filed on Jun. 21, 2021, the entire contents of which are incorporated herein by this reference.

BACKGROUND OF THE INVENTION

1. Field of the Invention

The present invention relates to an image pickup unit for endoscope that holds a barrel, in which an optical member is internally provided, to be movable into another barrel, and relates to an endoscope.

2. Description of the Related Art

An image pickup unit that picks up an optical image of a subject is provided at a distal end portion of an insertion section of an endoscope. As the image pickup unit, an image pickup unit including an optical system capable of moving a moving barrel, which holds an optical member, in an optical axis direction in a fixed barrel, has been proposed conventionally.

For example, Japanese Patent Application Laid-Open Publication No. 2018-66877 describes an image pickup apparatus for endoscope capable of switching a focus by holding a moving barrel, which holds at least a part of an optical system, in a holding barrel (a fixed barrel) to be movable in an optical axis direction of the optical system.

SUMMARY OF THE INVENTION

An image pickup unit for endoscope according to an aspect of the present invention includes: a first barrel having first hardness in which a hole is formed, a second barrel having second hardness in which an optical member is internally provided, the second barrel being held in the hole of the first barrel to be movable relative to the first barrel; a film having third hardness lower than the first hardness and the second hardness formed on one of an inner surface of the hole and an outer surface of the second barrel and configured to slide with another of the inner surface of the hole and the outer surface of the second barrel; in which the second barrel has a magnet or is composed by a magnetic material; and a coil provided in the first barrel and configured to generate a magnetic field that acts on the magnet or the magnetic material, in which the second barrel slides in the first barrel according to energization to the coil.

An endoscope according to an aspect of the present invention includes: an image pickup unit including: a first barrel having first hardness in which a hole is formed; a second barrel having second hardness in which an optical member is internally provided, the second barrel being held in the hole of the first barrel to be movable relative to the first barrel; a film having third hardness lower than the first hardness and the second hardness formed on one of an inner surface of the hole and an outer surface of the second barrel and configured to slide with another of the inner surface of the hole and the outer surface of the second barrel; in which the second barrel has a magnet or is composed by a magnetic material; and a coil provided in the first barrel and configured to generate a magnetic field that acts on the magnet or the magnetic material, the second barrel sliding in the first barrel according to energization to the coil; and an insertion section in which the image pickup unit is disposed, the insertion section being inserted into a subject.

DETAILED DESCRIPTION OF THE PREFERRED EMBODIMENTS

Figure 1:
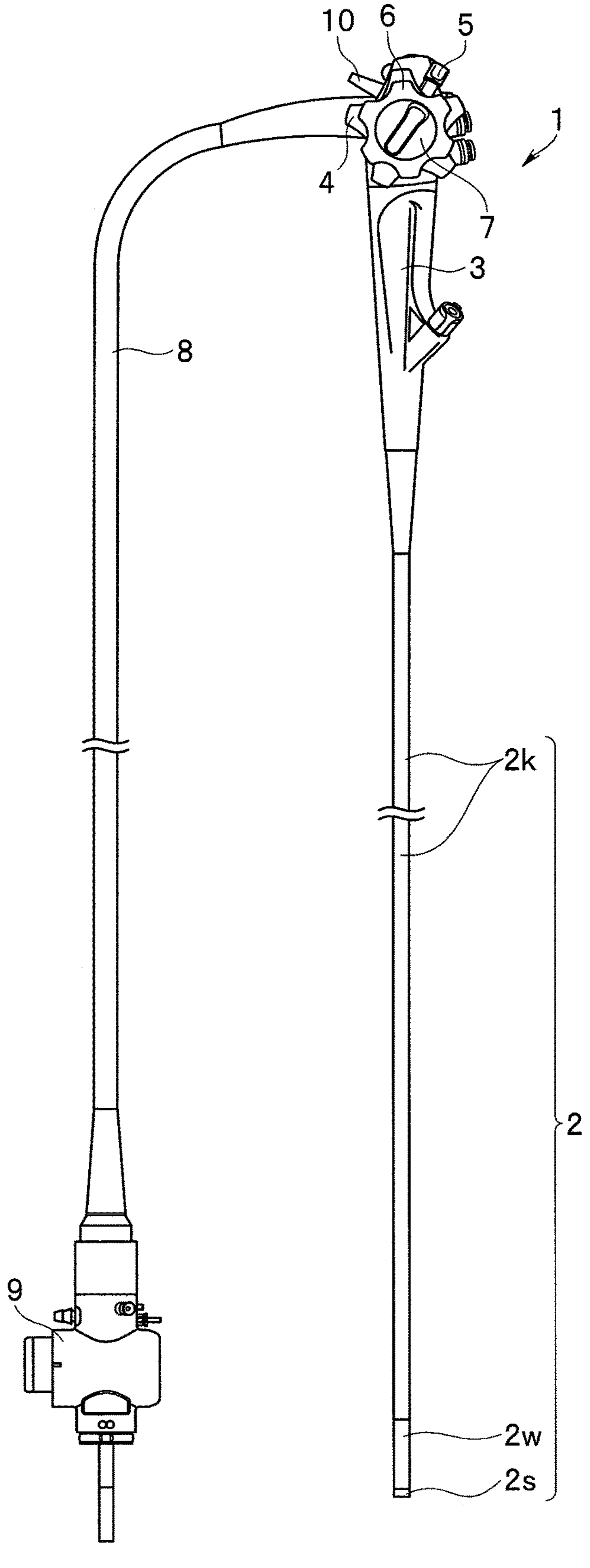
FIG. 1 is a diagram showing an exterior of an endoscope including an image pickup unit in a first embodiment of the present invention.

Embodiments of the present invention are explained below with reference to the drawings. However, the present invention is not limited by the embodiments explained below.

Note that, in the description of the drawings, the same or corresponding elements are denoted by the same reference numerals and signs as appropriate. It should be noted that the drawings are schematic and relations of lengths of respective elements, ratios of the lengths of the respective elements, quantities of the respective elements, and the like in one drawing are sometimes different from realities in order to simplify explanation. Further, portions, relations and ratios of lengths of which are different, are sometimes included among a plurality of drawings.

First Embodiment

FIG. 1 to FIG. 5 show a first embodiment of the present invention. FIG. 1 is a diagram showing an exterior of an endoscope 1 including an image pickup unit 11.

As shown in FIG. 1, the endoscope 1 includes an insertion section 2, an operation section 3, a universal cord 8, and a connector 9. The insertion section 2 is an elongated part inserted into a subject. The operation section 3 is connected consecutively to a proximal end side of the insertion section 2. The universal cord 8 is extended from, for example, a side surface on the proximal end side of the operation section 3. The connector 9 is provided at an extension end of the universal cord 8. The connector 9 electrically connects the endoscope 1 to not-shown external devices such as an endoscope processor and a light source device.

In the insertion section 2, a distal end portion 2*s*, a bending section 2*w*, and a flexible tube section 2*k* are connected consecutively in order from a distal end side.

The image pickup unit 11 explained below for picking up an optical image of a subject is disposed inside the distal end portion 2*s*. As explained below, the image pickup unit 11 in the present invention is configured to be capable of changing functions (zoom, focus, and the like) of an optical system. Consequently, the image pickup unit 11 can change magnification of a subject image.

A bending operation knob for performing operation for bending the bending section 2*w* is provided in the operation section 3. The bending operation knob includes an up-down bending operation knob 4 for performing operation for bending the bending section 2*w* in an up-down direction and a left-right bending operation knob 6 for performing operation for bending the bending section 2*w* in the left-right direction. The up-down bending operation knob 4 and the left-right bending operation knob 6 are connected to a bending piece at a distalmost end among a plurality of bending pieces connected consecutively in an inside of the bending section 2*w*, via a bending wire disposed in the insertion section 2.

When the up-down bending operation knob 4 and the left-right bending operation knob 6 are, for example, turned, the bending wire is towed and the bending section 2*w* bends in any combined direction of an upward or downward direction or a left or right direction. When the bending section 2*w* is bent, a direction of the distal end portion 2*s* changes and an observation direction of the image pickup unit 11 changes. The bending section 2*w* is also bent to improve insertion property of the distal end portion 2*s* in the subject.

A fixed lever 5 and a fixed knob 7 are provided in the operation section 3. The fixed lever 5 is used to fix a turning position of the up-down bending operation knob 4. The fixed knob 7 is used to fix a turning position of the left-right bending operation knob 6.

Further, an operation lever 10 for changing a function of an optical system of the image pickup unit 11 is provided in the operation section 3. When the operation lever 10 is operated, a moving barrel 30 explained below provided in the image pickup unit 11 moves in an optical axis O direction.

The flexible tube section 2*k* is an elongated tubular section having flexibility. Inside the flexible tube section 2*k*, the bending wire explained above, a light guide for transmitting illumination light received from a light source device to the distal end portion 2*s*, an electric cable for connecting the image pickup unit 11 to the endoscope processor, and the like are disposed.

Figure 2:
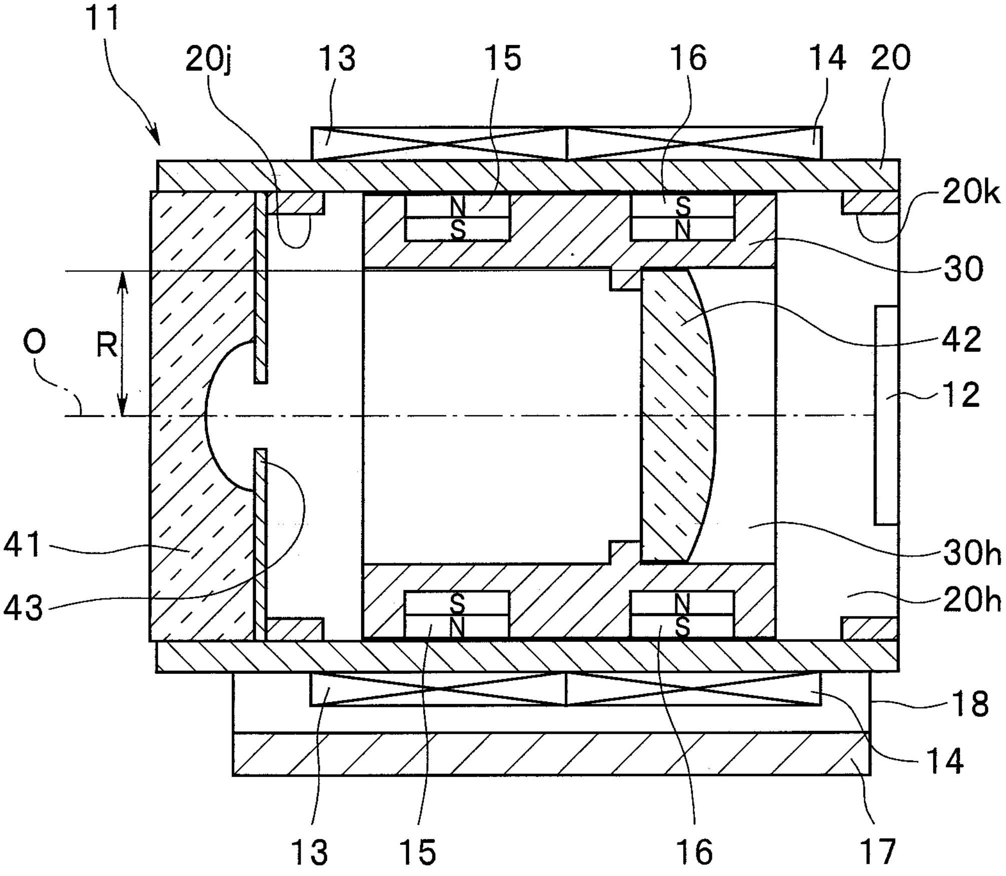
FIG. 2 is a sectional view taken along an optical axis of the image pickup unit in the first embodiment.

FIG. 2 is a sectional view taken along an optical axis of the image pickup unit 11.

The image pickup unit 11 includes an image pickup device 12, coils 13 and 14, magnets 15 and 16, a magnetic member 17, a holding member 18, a fixed barrel 20 (a first barrel), a moving barrel 30 (a second barrel), an objective lens 41, a moving lens 42, and an optical aperture 43.

The objective lens 41, the moving lens 42, and the optical aperture 43 configure an optical system that forms an optical image of a subject on the image pickup device 12.

The fixed barrel 20 is fixed in the distal end portion 2*s* and formed in a tubular shape including a hole 20*h* (a first hole) in a direction of an optical axis O of the optical system. More specifically, the fixed barrel 20 is formed in a cylindrical shape. A shape of the hole 20*h* is also a cylindrical shape. The objective lens 41 and the optical aperture 43 are fixed to a distal end portion of the hole 20*h* of the fixed barrel 20 in order from the distal end side. Note that, in FIG. 2, one objective lens 41 and one optical aperture 43 are disposed. However, a plurality of objective lenses and a plurality of optical apertures may be provided in the direction of the optical axis O.

A distal end side stopper 20*j* that restricts movement of the moving barrel 30 to the distal end side is provided adjacent to the proximal end side of the optical aperture 43 in the hole 20*h*. A proximal end side stopper 20*k* that restricts movement of the moving barrel 30 to the proximal end side is provided at an end portion on the proximal end side in the hole 20*h*.

The coil 13 and the coil 14 are disposed in different positions in the optical axis O direction on an outer circumferential surface of the fixed barrel 20 in order from the distal end side. The coils 13 and 14 configure an actuator that moves the moving barrel 30. The coil 13 and the coil 14 are wound in opposite directions. A direction of an electric current for energizing the coil 13 and a direction of an electric current for energizing the coil 14 are opposite.

The moving barrel 30 is formed in a tubular shape including a hole 30*h* (a second hole) in the optical axis O direction of the optical system. More specifically, the moving barrel 30 is formed in a cylindrical shape. The shape of the hole 30*h* is also a cylindrical shape. In the moving barrel 30, the moving lens 42 (an optical member) is disposed inside the hole 30*h*. Note that, in FIG. 2, one moving lens 42 is disposed. However, a plurality of moving lenses may be provided in the direction of the optical axis O.

The moving barrel 30 is held to be movable relative to the fixed barrel 20 between the distal end side stopper 20*j* and the proximal end side stopper 20*k* in the hole 20*h* of the fixed barrel 20. A moving direction of the moving barrel 30 with respect to the fixed barrel 20 is mainly the optical axis O direction. However, in order to enable the moving barrel 30 to move in the hole 20*h*, an outer diameter of the moving barrel 30 centering on the optical axis O is slightly smaller than an inner diameter of the fixed barrel 20 (a diameter of the hole 20*h*) and a gap is present between the fixed barrel 20 and the moving barrel 30. Therefore, the moving direction of the moving barrel 30 with respect to the fixed barrel 20 may include a direction perpendicular to the optical axis O. The moving direction of the moving barrel 30 with respect to the fixed barrel 20 may include a rotating direction around the optical axis O.

The magnet 15 and the magnet 16 are disposed on an outer circumference side of the moving barrel 30 in order from the distal end side. The magnets 15 and 16 configure an actuator that moves the moving barrel 30. A plurality of magnets 15 and 16 are provided at every constant angle, for example, four magnets 15 and 16 are provided at every 90° in a circumferential direction on the outer circumference side of the moving barrel 30. Note that surfaces on an outer diameter side of the magnets 15 and 16 may be disposed slightly further on an inner diameter side than an outer circumferential surface of the moving barrel 30 to prevent the magnets 15 and 16 from coming into contact with an inner circumferential surface of the fixed barrel 20. Instead of the magnets 15 and 16, the moving barrel 30 could be composed by a magnetic material.

The magnet 15 is magnetized to an S pole on the inner diameter side and magnetized to an N pole on the outer diameter side. The magnet 16 is magnetized to an N pole on the inner diameter side and magnetized to an S pole on the outer diameter side. Note that the magnet 15 and the magnet 16 only have to have opposite magnetization directions. Therefore, the magnet 15 may be magnetized to the N pole on the inner diameter side and magnetized to the S pole on the outer diameter side and the magnet 16 may be magnetized to the S pole on the inner diameter side and magnetized to the N pole on the outer diameter side.

The coil 13 explained above is provided in a movable range in the optical axis O direction of the magnet 15. The coil 14 is provided in a movable range in the optical axis O direction of the magnet 16. Therefore, the magnet 15 faces the coil 13 across the fixed barrel 20. The magnet 16 faces the coil 14 across the fixed barrel 20.

The coils 13 and 14 are energized to generate magnetic fields that act on the magnets 15 and 16 and generate a driving force for the moving barrel 30. The moving barrel 30 slides in the fixed barrel 20 according to the energization to the coils 13 and 14.

At this time, the magnetization directions of the magnet 15 and the magnet 16 are opposite. Therefore, by reversing a direction of an electric current for energizing the coil 13 and a direction of an electric current for energizing the coil 14, driving forces generated in the magnet 15 and the magnet 16 are in the same direction according to the Fleming's left hand rule.

When a direction of an electric current fed to the coils 13 and 14 (a driving current for moving the moving barrel 30) is reversed, a direction in which the moving barrel 30 moves along the optical axis O is reversed. Consequently, by switching the direction of the driving current, the moving direction of the moving barrel 30 along the optical axis O can be switched to a distal end direction and a proximal end direction. A focus of the optical system changes between when the moving barrel 30 is attached to the distal end side stopper 20*j* and when the moving barrel 30 is attached to the proximal end side stopper 20*k*. Consequently, a magnification changing mechanism that can change magnification of an optical image of a subject formed on the image pickup device 12 is configured.

The holding member 18 is fixed in a certain angle position in a circumferential direction of the outer circumferential surface of the fixed barrel 20. The holding member 18 holds the magnetic member 17 in a position separated from the outer circumferential surface of the fixed barrel 20 (and outer circumferential surfaces of the coils 13 and 14).

The magnetic member 17 is formed in, for example, an elongated flat plate shape in the optical axis O direction and applies an attractive force to any magnets 15 and 16 among the four magnets 15 and 16 provided in the circumferential direction. The moving barrel 30 is prevented from turning around the optical axis O by the attractive force of the magnetic member 17. The moving barrel 30 is attracted to a position near the magnetic member 17 in the hole 20*h* of the fixed barrel 20.

Figure 3:
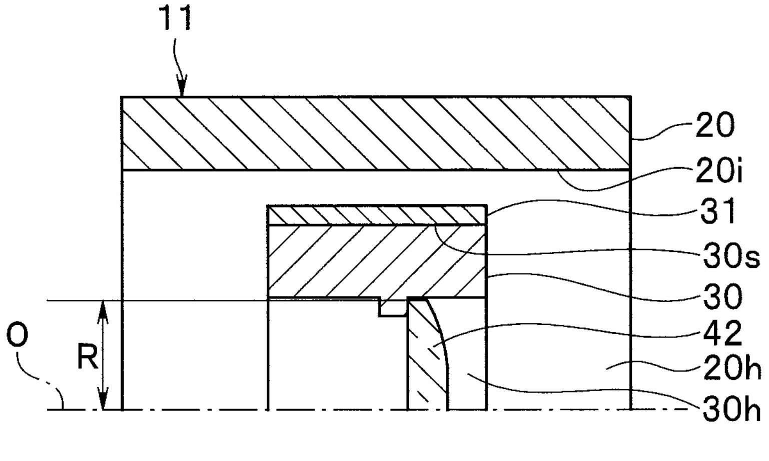
FIG. 3 is a diagram showing a configuration example in which a film is provided on an outer circumferential surface of a moving barrel in the image pickup unit in the first embodiment.
Figure 4:
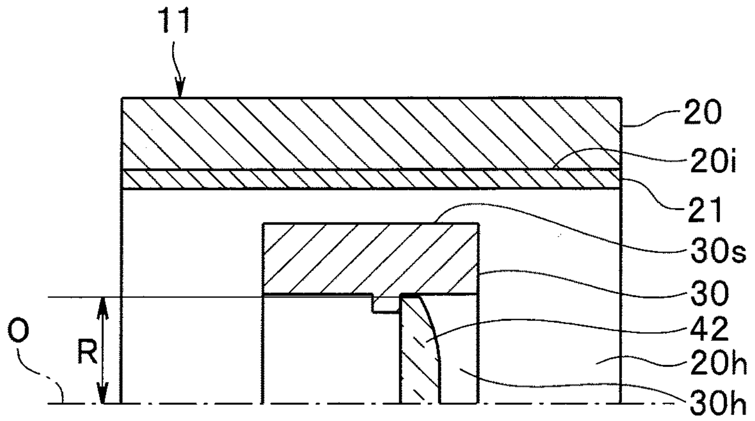
FIG. 4 is a diagram showing a configuration example in which a film is provided on an inner circumferential surface of a fixed barrel in the image pickup unit in the first embodiment.

Next, a configuration relating to sliding of the fixed barrel 20 and the moving barrel 30 is explained. FIG. 3 is a diagram showing a configuration example in which a film 31 is provided on an outer circumferential surface 30*s* (an outer surface) of the moving barrel 30 in the image pickup unit 11. FIG. 4 is a diagram showing a configuration example in which a film 21 is provided on an inner circumferential surface 20*i* (an inner surface) of the fixed barrel 20 in the image pickup unit 11.

The fixed barrel 20 is formed by a material having first hardness and the moving barrel 30 is formed by a material having second hardness. The first hardness and the second hardness do not need to be the same.

Here, to machine the moving barrel 30 and the fixed barrel 20 at high accuracy, it is efficient to form the moving barrel 30 and the fixed barrel 20 using the same material. Therefore, the second hardness is preferably the same as the first hardness. More specifically, examples of the material forming the fixed barrel 20 and the moving barrel 30 include stainless steel having high corrosion resistance. Further, it is desirable to use stainless steel, Vickers hardness of which is, for example, equal to or higher than approximately 180 HV, among kinds of stainless steel. By using the stainless steel having such hardness, it is possible to highly accurately form the fixed barrel 20 and the moving barrel 30 and it is possible to suppress optical axis deviation between the objective lens 41 and the moving lens 42 and a tilt of optical axes of the objective lens 41 and the moving lens 42 and prevent deterioration in image quality.

The film 31 (FIG. 3) or the film 21 (FIG. 4) is formed on one of the inner circumferential surface 20*i* of the hole 20*h* and the outer circumferential surface 30*s* of the moving barrel 30. The films 31 and 21 are formed by a material having third hardness lower than the first hardness and the second hardness. The film 31 shown in FIG. 3 slides with the inner circumferential surface 20*i* of the hole 20*h*. The film 21 shown in FIG. 4 slides on the outer circumferential surface 30*s* of the moving barrel 30.

The third hardness is preferably an order of magnitude smaller than the first hardness and the second hardness in Vickers hardness. The third hardness is preferably half or less of the first hardness and the second hardness and more preferably one third or less of the first hardness and the second hardness in Vickers hardness.

Here, the material forming the films 31 and 21 is required to be less easily ionized (oxidized) and have Vickers hardness an order of magnitude smaller and half to one third or less compared with the stainless steel explained above.

Examples of metal as such a material include a metal material containing a noble metal as a main component and having Vickers hardness of 90 HV or lower. Specific examples of noble metals having Vickers hardness of approximately 20 to 50 HV include gold (Au), silver (Ag), platinum (Pt), and palladium (Pd). Since the Vickers hardness of stainless steel is, for example, approximately 180 HV or higher as explained above, the Vickers hardness of 20 to 50 HV satisfies both of the hardness being an order of magnitude smaller and the hardness being one third or less.

The metal material containing the noble metal as the main component is cited as an example above. However, other soft metals may be used as the material of the films 31 and 21 as long as the metals are less easily ionized (oxidized) (less easily forms a compound) and have Vickers hardness of 90 HV or lower.

Examples of another material forming the films 31 and 21 include fluororesin. Examples of yet another material forming the films 31 and 21 include boron and a boron compound. Here, a specific example of the boron compound is boron nitride. Vickers hardness of these materials only has to be set to, for example, approximately 50 HV, although the Vickers hardness can be sometimes changed by heat treatment or the like.

The noble metal, the fluororesin, the boron, and the boron compound have a characteristic of not being chemically absorbed or being weak in chemical absorption. Therefore, in an endoscope used in a hot and humid environment, it is possible to prevent deterioration of the films 31 and 21 due to chemical bonding with moisture and oxygen in a periphery.

For example, when the endoscope 1 is ultrasonically cleaned, the fixed barrel 20 and the moving barrel 30 repeatedly slide with ultrasound vibration and fretting occurs. It is known that surface damage (mechanical deterioration) due to the fretting is caused by friction and a frictional force F is practically F=(shear strength of surface)×(real contact area). Here, a surface of an object has very small unevenness, although seen smooth at a glance. Two objects are mainly brought into contact in very small projections of the objects. The real contact area indicates not an apparent area of a portion in contact but an area of a portion actually in contact.

To suppress the surface damage, it is effective to reduce the frictional force F. To reduce the frictional force F, it is desirable to perform one or preferably both of (1) and (2) described below.

(1) Reduce the shear strength of the surface (2) Reduce the real contact area

Therefore, in the present embodiment, in order to achieve (1), the films 31 and 21 are formed by the material (a soft material) having hardness lower than the hardness of the material forming the fixed barrel 20 and the moving barrel 30 and are formed as soft films.

In order to achieve (2), the stainless steel having Vickers hardness of, for example, approximately 180 HV or higher is used as the material forming the fixed barrel 20 and the moving barrel 30. When the fixed barrel 20 and the moving barrel 30 are formed of a hard material and the soft films 31 and 21 are formed by plating, vapor deposition, or the like, thickness of the films 31 and 21 becomes substantially uniform. Then, an unevenness shape on surfaces of the moving barrel 30 and the fixed barrel 20 is substantially maintained on the films 31 and 21 as well. Therefore, the real contact area can be reduced.

It has been experimentally confirmed as well that, by satisfying (1) and (2), it is possible to prevent damage to the surface from easily occurring. For example, a change in a value of a coefficient of dynamic friction in the case in which the soft films 31 and 21 are formed on a hard member and thickness of the films 31 and 21 is changed has been checked by an experiment. As a result of the experiment, the value of the coefficient of dynamic friction is minimized at specific thickness and increases regardless of whether the thickness of the films 31 and 21 is larger or smaller than the specific thickness.

If the films 31 and 21 are too thin, when the endoscope 1 is repeatedly used, a period in which the endoscope 1 can be used as a product decreases. Technical difficulty increases when film thickness of less than 0.1 m is formed.

Conversely, if the films 31 and 21 are too thick, a ratio of a load shared by the films 31 and 21 with the moving barrel 30 and the fixed barrel 20 increases. If the films 31 and 21 are thick, tolerance to the thickness also increases. The large tolerance to the thickness of the films 31 and 21 causes eccentricity variation of the moving barrel 30 and becomes a factor of image quality deterioration. Film thickness with which the tolerance is within an allowable range of a product is, for example, 10 μm or less.

Considering the above, it is preferable that the thickness of the films 31 and 21 formed on the moving barrel 30 or the fixed barrel 20 be, for example, 0.1 μm or more and 10 μm or less. Examples of particularly preferable thickness of the films 31 and 21 include 1 μm.

Figure 5:
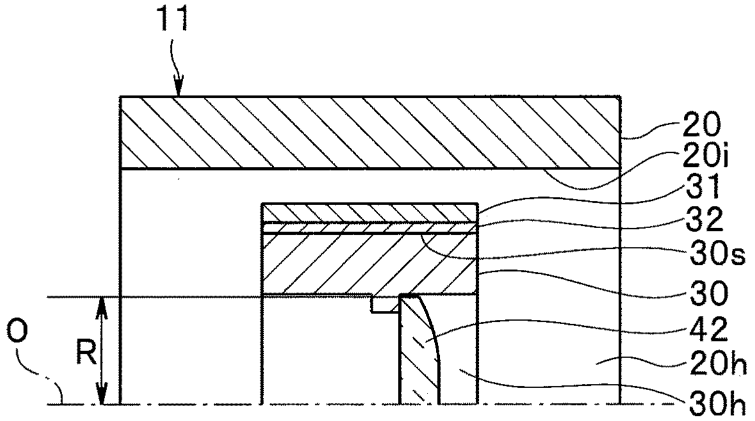
FIG. 5 is a diagram showing a configuration example in which an intermediary material and a film are provided on the outer circumferential surface of the moving barrel in the image pickup unit in the first embodiment.

FIG. 5 is a diagram showing a configuration example in which an intermediary material 32 and the film 31 are provided on the outer circumferential surface 30*s* of the moving barrel 30 in the image pickup unit 11.

In the example shown in FIG. 3, the film 31 is directly provided on the outer circumferential surface 30*s* of the moving barrel 30. However, as shown in FIG. 5, the intermediary material 32 may be provided on the outer circumferential surface 30*s* of the moving barrel 30 and the film 31 may be provided on the intermediary material 32. Here, the intermediary material 32 is a film that more firmly bonds the moving barrel 30 and the film 31 (improves adhesion) and is formed by plating, vapor deposition, or the like. A specific example of a material forming the intermediary material 32 is nickel (Ni).

Figure 6:
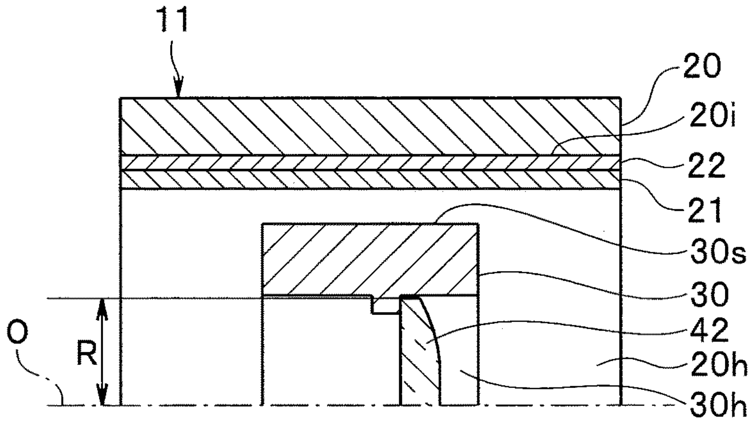
FIG. 6 is a diagram showing a configuration example in which an intermediary material and a film are provided on the inner circumferential surface of the fixed barrel in the image pickup unit in the first embodiment.

FIG. 6 is a diagram showing a configuration example in which an intermediary material 22 and the film 21 are provided on the inner circumferential surface 20*i* of the fixed barrel 20. It goes without saying that the intermediary material 22 of nickel or the like may be used when the film 21 is provided on the inner circumferential surface 20*i* of the fixed barrel 20.

As shown in FIG. 3 to FIG. 5, the inner circumferential surface 20*i* of the hole 20*h* and the outer circumferential surface 30*s* of the moving barrel 30 are located further on an outer side than a radius R of the moving lens 42 centering on the optical axis O of the moving lens 42. Therefore, the films 31 and 21 are also formed further on the outer side than the radius R of the moving lens 42 centering on the optical axis O.

According to the first embodiment explained above, since the film 21 or the film 31 lower in hardness than the fixed barrel 20 and the moving barrel 30 is provided in one of the inner circumferential surface 20*i* of the fixed barrel 20 and the outer circumferential surface 30*s* of the moving barrel 30, fretting can be suppressed. Since the fretting is suppressed, occurrence of abrasion powder is suppressed and deterioration in image quality can be prevented.

It is possible to suppress, without using a lubricant, fretting of the fixed barrel 20 and the moving barrel 30, for example, in the case in which the endoscope 1 is ultrasonically cleaned by a cleaning device. Therefore, it is possible to change magnification of a subject image without increasing a driving current for moving the moving barrel 30.

Further, since a lubricant is not used, easiness of assembly of the image pickup unit 11 is improved. The image pickup unit 11 is configured to be suitable for, for example, a single-use endoscope as well.

Since the fixed barrel 20 and the moving barrel 30 are formed of the same material (that is, a material having the same hardness), highly accurate machining can be efficiently performed.

Since the Vickers hardness of the films 31 and 21 is set an order of magnitude smaller than the Vickers hardness of the fixed barrel 20 and the moving barrel 30 and a value of the Vickers hardness of the films 31 and 21 is set to be half or less of a value of the Vickers hardness of the fixed barrel 20 and the moving barrel 30, it is possible to reduce a frictional force due to sliding to a practical level.

Since the films 31 and 21 are formed using the noble metal, the fluororesin, the boron, or the boron compound as the material, it is possible to prevent deterioration due to chemical bonding with moisture and oxygen in a periphery.

It is possible to suppress a decrease in a life (a usable period) of the image pickup unit 11 due to repeated sliding in a deteriorated state.

Since the metal material containing the noble metal as the main component is chemically stable among kinds of soft metal, durability other than sliding resistance of the films 31 and 21, for example, durability to chemicals is also improved.

Similarly, when the fluororesin, the boron, or the boron compound is used as the material of the films 31 and 21, hydrolysis and the like can be prevented.

Since the intermediary material 32 is provided between the moving barrel 30 or the fixed barrel 20 and the films 31 and 21, it is possible to improve adhesion of the films 31 and 21 and prevent peeling of the films 31 and 21. At this time, machining by plating or the like is facilitated by using nickel as a material of the intermediary material 32.

Since the thickness of the films 31 and 21 is set to 0.1 μm or more and 10 μm or less, it is possible to achieve both of extension of a sliding life and improvement of image quality.

Since the films 31 and 21 are provided further on the outer side than the radius R of the moving lens 42 centering on the optical axis O, it is possible to prevent light reflected by the films 31 and 21 from being made incident on the moving lens 42 and it is possible to suppress deterioration in image quality due to the reflected light.

Second Embodiment

Figure 7:
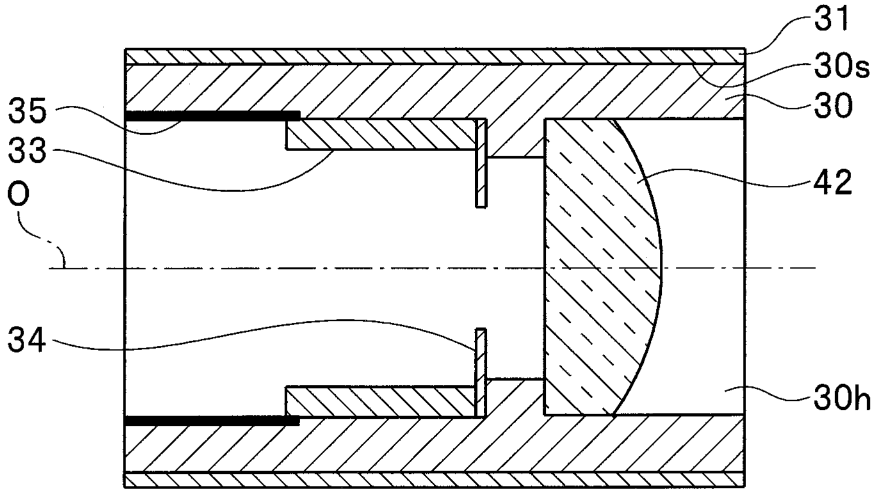
FIG. 7 is a diagram showing a configuration example of a moving barrel in a second embodiment of the present invention.

FIG. 7 shows a second embodiment of the present invention and is a diagram showing a configuration example of the moving barrel 30. In the second embodiment, explanation about the same portions as the portions in the first embodiment explained above is omitted as appropriate by, for example, adding the same reference numerals and signs to the portions. Only differences from the first embodiment are mainly explained.

In the example shown in FIG. 3 or FIG. 5 in the first embodiment, the film 31 is provided on the outer circumferential surface 30*s* of the moving barrel 30. However, when the film 31 is formed by plating or vapor deposition, it is technically difficult to form the film 31 only on the outer circumferential surface 30*s*. When the film 31 is formed of, for example, a metal material, reflectance of light is relatively high.

Therefore, in the present embodiment, even if a part of the film 31 is formed in the hole 30*h* of the moving barrel 30, reflection of a light beam by the film 31 is prevented.

More specifically, as shown in FIG. 7, a film removed section 35 subjected to treatment for removing the film 31 is formed, for example, on a distal end side (a left side along the optical axis O in FIG. 7 is the distal end side where the objective lens 41 is disposed) of the hole 30*h* in the moving barrel 30 in which the film 31 is formed on the outer circumferential surface 30*s*. The removal of the film 31 is performed by an appropriate method such as polishing or etching.

A low reflection member 33 is fixed to a portion adjacent to a proximal end side of the film removed section 35 in the hole 30*h* of the moving barrel 30. The low reflection member 33 is a member having reflectance of light lower than the reflectance of the films 31 and 21. The low reflection member 33 is, for example, a thin member formed in a cylindrical shape. The low reflection member 33 is not limited to be configured as an independent member and may be formed by, for example, reflection prevention coating.

An unnecessary-light blocking member 34 is fixed to a portion adjacent to the proximal end side of the low reflection member 33 in the hole 30*h* of the moving barrel 30. The unnecessary-light blocking member 34 is a member that allows light used for forming a subject image to pass and blocks light not used for forming the subject image (unnecessary light). The unnecessary-light blocking member 34 is, for example, a flat torus-shaped member, in a center portion of which a hole for allowing necessary light to pass is formed, and is formed in a shape similar to an aperture.

In the example shown in FIG. 7, the film removed section 35, the low reflection member 33, and the unnecessary-light blocking member 34 are provided in the hole 30*h* of the moving barrel 30. However, not all of the film removed section 35, the low reflection member 33, and the unnecessary-light blocking member 34 need to be provided and at least one of the film removed section 35, the low reflection member 33, or the unnecessary-light blocking member 34 only has to be provided.

In the example shown in FIG. 7, the film removed section 35, the low reflection member 33, and the unnecessary-light blocking member 34 are provided only on a distal end side of the moving lens 42. This is because the distal end side is a side on which light is made incident and a high effect is obtained if the film removed section 35, the low reflection member 33, and the unnecessary-light blocking member 34 are provided on the distal end side. However, not only this, but at least one of the film removed section 35, the low reflection member 33, or the unnecessary-light blocking member 34 may be provided on the proximal end side of the moving lens 42.

According to the second embodiment explained above, substantially the same effects as the effects in the first embodiment explained above are achieved. In addition, by providing at least one of the film removed section 35, the low reflection member 33, or the unnecessary-light blocking member 34 in the hole 30*h* of the moving barrel 30 in which the film 31 is formed on the outer circumferential surface 30*s*, it is possible to reduce unnecessary light made incident on the image pickup device 12. Consequently, it is possible to reduce optical noise such as flare and ghost and improve quality of an image.

Third Embodiment

Figure 8:
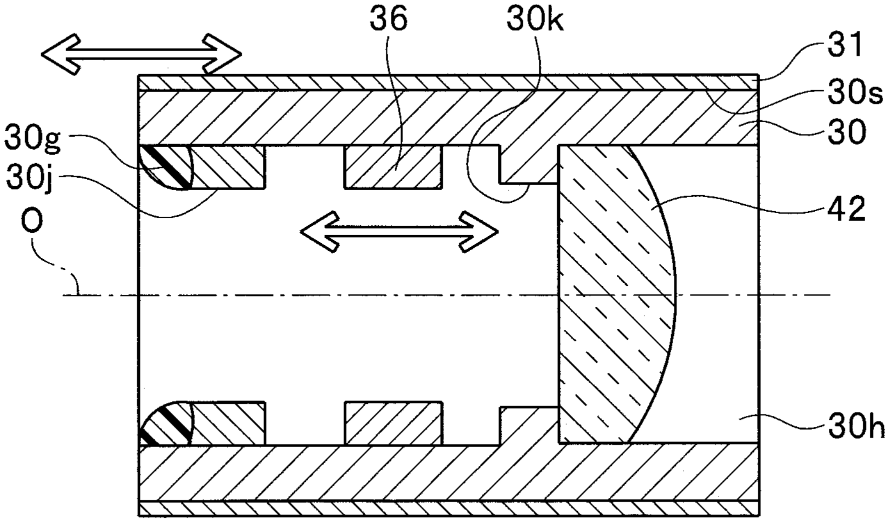
FIG. 8 is a diagram showing a configuration example of a moving barrel in a third embodiment of the present invention.

FIG. 8 shows a third embodiment of the present invention and is a diagram showing a configuration example of the moving barrel 30. In the third embodiment, explanation about the same portions as the portions in the first and second embodiments explained above is omitted as appropriate by, for example, adding the same reference numerals and signs to the portions. Only differences from the first and second embodiments are mainly explained.

An annular member 36 movable in a direction of the optical axis O is further disposed inside the hole 30*h* of the moving barrel 30 in the present embodiment. A center portion of the annular member 36 is formed as a hole for allowing light used for forming a subject image to pass.

The moving barrel 30 includes a proximal end side stopper 30*k* projected in an inner diameter direction from the hole 30*h*. The proximal end side stopper 30*k* functions as, for example, a positioning member in the optical axis O direction of the moving lens 42 as well.

A distal end side stopper 30*j* is fixed to a distal end side of the hole 30*h* of the moving barrel 30 using, for example, an adhesive 30*g*. The distal end side stopper 30*j* is fixed by the adhesive 30*g* after the annular member 36 is disposed inside the hole 30*h*.

In such a configuration, the annular member 36 is movable in a direction of the optical axis O between the distal end side stopper 30*j* and the proximal end side stopper 30*k*. Note that even if the annular member 36 moves in the direction of the optical axis O, the annular member 36 does not block light used for forming a subject image. Therefore, image quality is not affected.

When the endoscope 1 is ultrasonically cleaned by a cleaning device, the moving barrel 30 vibrates in the optical axis O direction relative to the fixed barrel 20. When the moving barrel 30 vibrates in the optical axis O direction, the annular member 36 is also about to vibrate in the optical axis O direction with sliding resistance against the moving barrel 30. However, a phase of the vibration of the annular member 36 deviates from a phase of the vibration of the moving barrel 30 (for example, the phase is delayed). Consequently, the annular member 36 functions as a vibration control mechanism for the moving barrel 30. Amplitude, speed, the number of times, and the like of very small high-speed vibration of the moving barrel 30 are suppressed.

Note that, for the annular member 36 to function as the vibration control mechanism, a certain degree of weight that can be compared with weight of the moving barrel 30 is necessary. Therefore, the annular member 36 desirably has a configuration in which load bodies are disposed in a plurality of parts in equal angle positions around the optical axis O, for example, on an inner circumference side of fluororesin formed in a ring shape.

According to the third embodiment explained above, substantially the same effects as the effects in the first and second embodiments explained above are achieved. In addition, since the annular member 36 is provided inside the hole 30*h* of the moving barrel 30, it is possible to suppress amplitude, speed, the number of times, and the like of vibration of the moving barrel 30 at a time when the endoscope 1 is ultrasonically cleaned and it is possible to reduce a load applied to the image pickup unit 11 by the ultrasonic cleaning. Consequently, it is possible to suppress deterioration of the image pickup unit 11 and extend a life of the image pickup unit 11.

Fourth Embodiment

Figure 9:
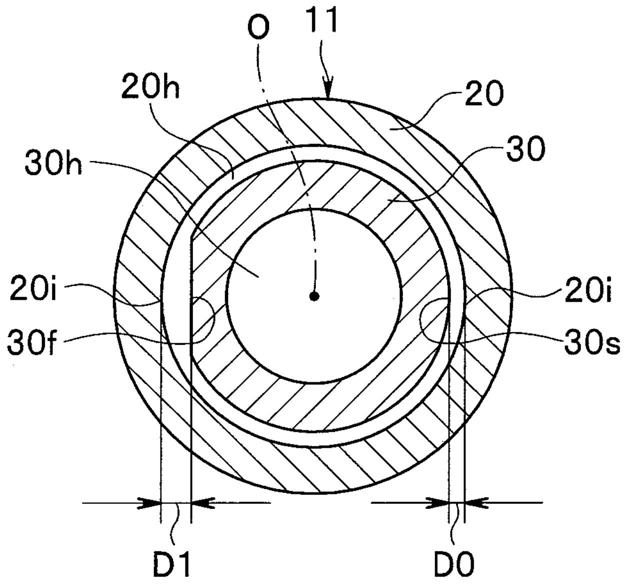
FIG. 9 is a diagram showing a configuration example of an image pickup unit in a fourth embodiment of the present invention.
Figure 10:
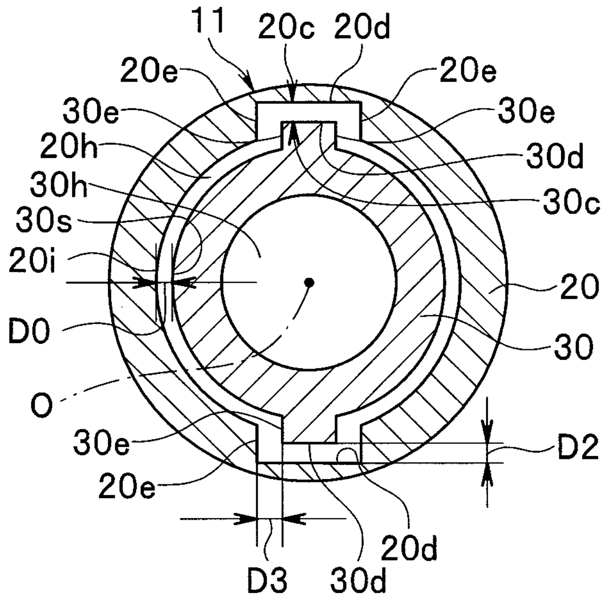
FIG. 10 is a diagram showing another configuration example of the image pickup unit in the fourth embodiment of the present invention.

FIG. 9 and FIG. 10 show a fourth embodiment of the present invention. FIG. 9 is a diagram showing a configuration example of the image pickup unit 11. In the fourth embodiment, explanation about the same portions as the portions in the first to third embodiments explained above is omitted as appropriate by, for example, adding the same reference numerals and signs to the portions. Only differences from the first to third embodiments are mainly explained.

In the configuration example shown in FIG. 9, a flat shape section 30*f* is provided in a part in a circumferential direction of the outer circumferential surface 30*s* formed in a cylindrical shape of the moving barrel 30. The flat shape section 30*f* only has to be provided in at least a part in the optical axis O direction (preferably, at least one of both end portions in the optical axis O direction) of the outer circumferential surface 30*s* and does not need to be provided over the entire outer circumferential surface 30*s* in the optical axis O direction.

It is assumed that, at a time of disposition in which both of a center axis of the moving barrel 30 and a center axis of the fixed barrel 20 are made to coincide with the optical axis O, an interval of a gap between the outer circumferential surface 30*s* formed in a cylindrical shape and the inner circumferential surface 20*i* formed in a cylindrical shape is DO. The moving barrel 30 is configured such that an interval D1 of a gap between the flat shape section 30*f* and the inner circumferential surface 20*i* is larger than D0 at this time.

Note that, in the present embodiment as well, the film 31 is formed on the outer circumferential surface 30*s* of the moving barrel 30 or the film 21 is formed on the inner circumferential surface 20*i* of the fixed barrel 20. However, illustration of the film 31 and the film 21 is omitted in FIG. 9 and FIG. 10.

FIG. 10 is a diagram showing another configuration example of the image pickup unit 11.

In the configuration example shown in FIG. 10, for example, two convex sections 30*c* are provided on the outer circumferential surface 30*s* formed in the cylindrical shape. The two convex sections 30*c* are projected in an outer diameter direction from the outer circumferential surface 30*s* in 1800 positions in a circumferential direction of the outer circumferential surface 30*s*. Surfaces on an outer diameter side of the convex sections 30*c* are formed as flat shape sections 30*d* and both side surfaces of the convex sections 30*c* are formed as flat shape sections 30*e*.

Two concave sections 20*c* for the two convex sections 30*c* explained above to enter are provided on the inner circumferential surface 20*i* formed in the cylindrical shape. Surfaces on the outer diameter side (concave bottom surfaces) of the concave sections 20*c* are formed as flat shape sections 20*d* and both side surfaces of the concave sections 20*c* are formed as flat shape sections 20*e*.

Note that the convex sections 30*c* and the concave sections 20*c* only have to be provided in at least parts in the optical axis O direction (preferably, at least one of both end portions in the optical axis O direction) of the outer circumferential surface 30*s* and the inner circumferential surface 20*i* and do not need to be provided over the entire outer circumferential surface 30*s* and the entire inner circumferential surface 20*i* in the optical axis O direction. The convex sections 30*c* and the concave sections 20*c* are not limited to be the two convex sections 30*c* and the two concave sections 20*c* provided in the circumferential direction. One or three or more convex sections 30*c* and one or three or more concave sections 20*c* may be provided.

It is assumed that, at a time of disposition in which both of the center axis of the moving barrel 30 and the center axis of the fixed barrel 20 are made to coincide with the optical axis O, the interval of the gap between the outer circumferential surface 30*s* formed in the cylindrical shape and the inner circumferential surface 20*i* formed in the cylindrical shape is DO. An interval of a gap between the flat shape section 20*d* and the flat shape section 30*d* at a time when the convex sections 30*c* are located in the centers of the concave sections 20*c* in the circumferential direction is represented as D2 and an interval of a gap between the flat shape section 20*e* and the flat shape section 30*e* at the time when the convex sections 30*c* are located in the centers of the concave sections 20*c* in the circumferential direction is represented as D3. The fixed barrel 20 and the moving barrel 30 are configured such that D2 is larger than DO and D3 is larger than DO at this time.

In the endoscope 1, it is desired that the insertion section 2 is reduced in diameter in order to improve insertion property. Therefore, the moving barrel 30 of the image pickup unit 11 has a small size. It is technically difficult to form the film 31 having equal thickness. If the film 31 having equal thickness cannot be formed, a part where deterioration due to sliding is concentrated occurs and the life of the image pickup unit 11 decreases.

To form the film 31 having equal thickness in the small moving barrel 30, it is desirable that a part for grasping the moving barrel 30 or a part for fixing the moving barrel 30 to a jig is present. If such a part (hereinafter referred to as specific shape section) is present, when the film 31 is formed by vapor deposition, the film 31 can be disposed in an appropriate layout in a vapor deposition kiln. When the film 31 is formed by plating, the film 31 can be prevented from being washed away by a liquid flow in plating liquid. It is easy to manage a work process.

By providing the flat shape section 30*f* shown in FIG. 9 or the flat shape sections 30*d* and 30*e* shown in FIG. 10 as explained above, it is possible to use the flat shape sections 30*d*, 30*e*, and 30*f* as the part for grasping the moving barrel 30 or the part for fixing the moving barrel 30 to a jig.

However, the specific shape section is, for example, grasped or fixed to a jib in a process for forming the film 31, the same film 31 as a film in a portion other than the specific shape section is not formed. Therefore, the specific shape section is requested not to come into contact with the inner circumferential surface 20*i* of the fixed barrel 20 or not always come into contact with the inner circumferential surface 20*i*. Therefore, the intervals D1, D2, and D3 of a gap of the specific shape section are configured to be larger than the interval DO of gaps of sections other than the specific shape section.

For example, the flat shape section 30*f* does not basically come into contact with the inner circumferential surface 20*i*. The flat shape section 30*d* also does not basically come into contact with the flat shape section 20*d*. Further, when the moving barrel 30 turns around the optical axis O, even if the flat shape section 30*e* temporarily comes into contact with the flat shape section 20*e*, the flat shape section 30*e* does not always come into contact with the flat shape section 20*e*. Therefore, even if the specific shape section is provided, friction at the time when the specific shape section slides does not basically increase. Movement of the moving barrel 30 is not hindered.

According to the fourth embodiment explained above, substantially the same effects as the effects in the first to third embodiments explained above are achieved and, since the flat shape section 30*f* is provided in the moving barrel 30 or the flat shape sections 30*d* and 30*e* are provided in the moving barrel 30 and the flat shape sections 20*d* and 20*e* are provided in the fixed barrel 20, the film 31 having equal thickness can be formed in the small moving barrel 30. Consequently, it is possible to implement the image pickup unit 11 having a long sliding life.

Note that the present invention is not limited to the embodiments explained above per se. In an implementation stage, constituent elements can be modified and embodied in a range not departing from the gist of the invention. Aspects of various inventions can be formed by appropriate combinations of a plurality of constituent elements disclosed in the embodiments. For example, several constituent elements may be deleted from all the constituent elements described in the embodiments. Further, constituent elements described in different embodiments may be combined as appropriate. As explained above, it goes without saying that various modifications and applications are possible within a range not departing from the gist of the invention.

What is claimed is:

1. An image pickup unit for an endoscope having suppressed fretting during ultrasonic cleaning comprising:

a first barrel having first hardness in which a hole is formed;

a second barrel having second hardness in which an optical member is internally provided, the second barrel being held in the hole of the first barrel to be movable relative to the first barrel, wherein the first barrel and second barrel comprise a stainless steel having a Vickers hardness of 180 HV or higher;

a film having third hardness lower than the first hardness and the second hardness formed on one of an inner surface of the hole and an outer surface of the second barrel and configured to slide with another of the inner surface of the hole and the outer surface of the second barrel, wherein the film has a Vickers hardness an order of magnitude lower and one third or less than the Vickers hardness of the first and second barrels;

wherein the second barrel has a magnet or is composed by a magnetic material; and a coil provided in the first barrel and configured to generate a magnetic field that acts on the magnet or the magnetic material, wherein the second barrel slides in the first barrel according to energization to the coil, wherein, when the endoscope is ultrasonically cleaned, fretting is suppressed.

2. The image pickup unit for an endoscope according to claim 1, wherein the third hardness is half or less of the first hardness and the second hardness in Vickers hardness.

3. The image pickup unit for an endoscope according to claim 1, wherein the second hardness is same as the first hardness.

4. The image pickup unit for an endoscope according to claim 1, wherein the film is formed by a metal material containing a noble metal as a main component and having Vickers hardness of 90 HV or lower.

5. The image pickup unit for an endoscope according to claim 1, wherein the film is formed by fluororesin.

6. The image pickup unit for an endoscope according to claim 1, wherein the film is formed by boron or a boron compound.

7. The image pickup unit for an endoscope according to claim 1, wherein an intermediary material for bonding one of the inner surface of the hole and the outer surface of the second barrel on which the film is formed and the film is further provided between the one and the film.

8. The image pickup unit for an endoscope according to claim 7, wherein the intermediary material is formed by nickel.

9. The image pickup unit for an endoscope according to claim 1, wherein thickness of the film is 0.1 μm or more and 10 μm or less.

10. The image pickup unit for an endoscope according to claim 1, wherein one of the inner surface of the hole and the outer surface of the second barrel on which the film is formed is located further on an outer side than a radius of the optical member centering on an optical axis of the optical member.

11. The image pickup unit for an endoscope according to claim 1, wherein the optical member is disposed inside a second hole formed in the second barrel, and the image pickup unit further comprises a low reflection member fixed to an inner surface of the second hole and having reflectance of light lower than reflectance of the film.

12. The image pickup unit for an endoscope according to claim 1, wherein the optical member is disposed inside a second hole formed in the second barrel, and the image pickup unit further comprises an annular member disposed inside the second hole and movable in a direction of an optical axis of the optical member.

13. The image pickup unit for an endoscope according to claim 1, wherein the outer surface of the second barrel includes a flat shape section, and a gap between the flat shape section and the inner surface of the hole is larger than a gap between the outer surface of the second barrel other than the flat shape section and the inner surface of the hole.

14. An endoscope having suppressed fretting during ultrasonic cleaning comprising:

an image pickup unit including:

a first barrel having first hardness in which a hole is formed;

a second barrel having second hardness in which an optical member is internally provided, the second barrel being held in the hole of the first barrel to be movable relative to the first barrel, wherein the first barrel and second barrel comprise a stainless steel having a Vickers hardness of 180 HV or higher;

a film having third hardness lower than the first hardness and the second hardness formed on one of an inner surface of the hole and an outer surface of the second barrel and configured to slide with another of the inner surface of the hole and the outer surface of the second barrel, wherein the film has a Vickers hardness an order of magnitude lower and one third less than the Vickers hardness of the first and second barrels;

wherein the second barrel has a magnet or is composed by a magnetic material; and a coil provided in the first barrel and configured to generate a magnetic field that acts on the magnet or the magnetic material, the second barrel sliding in the first barrel according to energization to the coil, and an insertion section in which the image pickup unit is disposed, the insertion section being inserted into a subject, wherein, when the endoscope is ultrasonically cleaned, fretting is suppressed.

* * * * *